United States Patent [19]

Johns

[11] Patent Number: 4,915,227

[45] Date of Patent: * Apr. 10, 1990

[54] ONE STEP DRESSING DELIVERY SYSTEM

[75] Inventor: Owen L. Johns, Madeira Beach, Fla.

[73] Assignee: Smith & Nephew United, Inc., Largo, Fla.

[*] Notice: The portion of the term of this patent subsequent to Nov. 1, 2005 has been disclaimed.

[21] Appl. No.: 387,179

[22] Filed: Jul. 28, 1989

Related U.S. Application Data

[63] Continuation of Ser. No. 228,074, Aug. 4, 1988, which is a continuation of Ser. No. 137,218, Dec. 23, 1987, Pat. No. 4,781,293.

[51] Int. Cl.4 ............... A61F 15/00; B65D 85/67
[52] U.S. Cl. ................... 206/441; 128/156
[58] Field of Search ............ 53/170, 425, 429, 450; 128/155, 156; 206/438–441, 460

[56] References Cited

U.S. PATENT DOCUMENTS

| 2,889,039 | 6/1959 | Schladermundt et al. | 206/441 |
|---|---|---|---|
| 2,946,435 | 7/1960 | Schladermundt et al. | 206/441 |
| 2,969,144 | 1/1961 | Zackheim | 206/441 |
| 2,969,145 | 1/1961 | Hannauer, Jr. | 206/441 |
| 3,018,881 | 1/1962 | Wall | 206/441 |
| 3,313,405 | 4/1967 | Blackford | 206/441 |
| 3,645,835 | 2/1972 | Hodgson | 428/355 |
| 4,182,449 | 1/1980 | Kozlow | 206/441 |
| 4,264,008 | 4/1981 | Kozlow | 206/441 |
| 4,304,333 | 12/1981 | Kozlow | 206/441 |
| 4,513,739 | 4/1985 | Johns | 128/156 |
| 4,781,293 | 11/1988 | Johns | 206/441 |

Primary Examiner—Jimmy G. Foster
Attorney, Agent, or Firm—Jacobs & Jacobs

[57] ABSTRACT

A dressing delivery system comprising an adhesive-coated dressing, a release liner and a package are arranged such that the package acts as the means for applying the dressing to a skin area, with the opening of the package and the application of the dressing being accomplished in a single step. A simple method of preparing the dressing delivery system is also described.

12 Claims, 4 Drawing Sheets

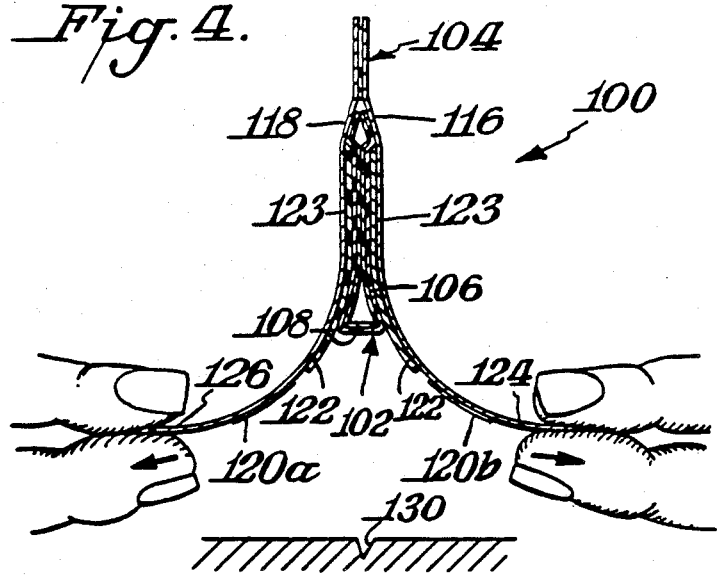
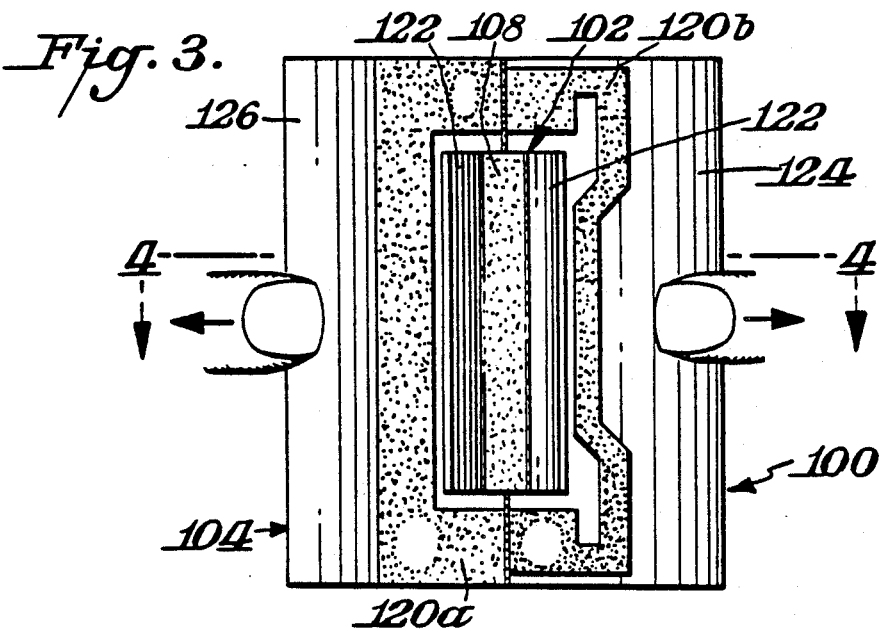
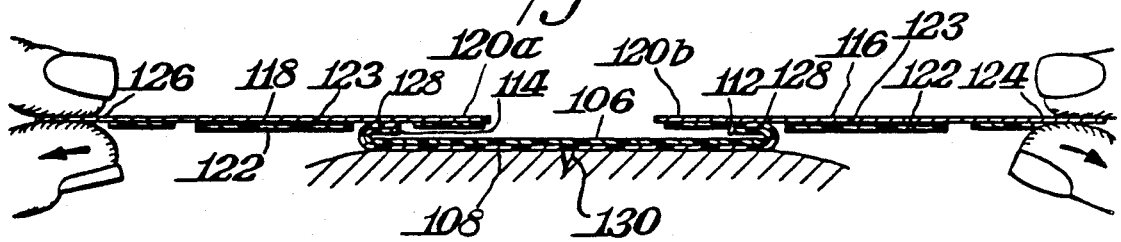

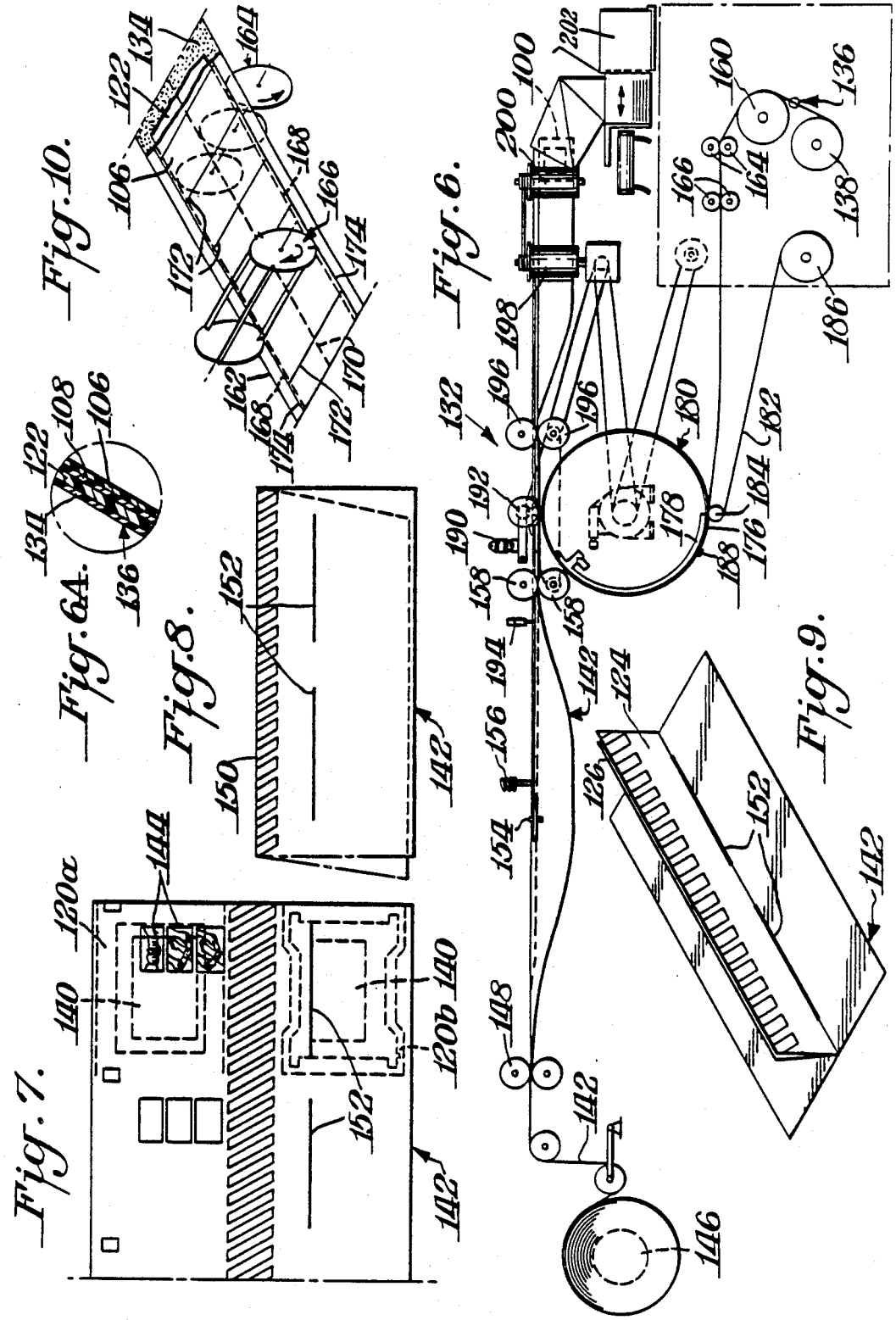

4,915,227

ONE STEP DRESSING DELIVERY SYSTEM

CROSS-REFERENCE

This is a continuation of Serial No. 228,074 filed August 4, 1988 which is a continuation of my application Serial No. 137,218 filed December 23, 1987 now U.S. Pat. No. 4,781,293

BACKGROUND OF THE INVENTION

This invention concerns a dressing delivery system in which the package for the dressing acts as the means for applying the dressing to a skin area.

Wound dressings are commonly supplied inside a package separate from the dressing, the package serving primarily to maintain sterility of the dressing prior to its application on a skin wound. With such dressings, the adhesive side of the dressing is protected by a release liner which is removed at the time of application.

Previous attempts have been made to provide a more efficient dressing delivery system by incorporating the package as a part of the system. U.S. Pat. No. 4,182,449, for example, discloses an adhesive bandage and package in which the package serves as a means of applying the bandage to a wound. In this system, an adhesive bandage comprising a backing layer with a pressure-sensitive adhesive layer and central pad on one surface is partially covered with a first cover sheet such that the pad is covered and one side of the adhesive surface is releasably attached to the sheet. The partially covered bandage is placed between a pair of second cover sheets slightly larger than the bandage which are releasably sealed around the periphery to provide a sealed package with peel tabs at the end of the bandage adjacent the partially covered portion of the bandage. To use the bandage, the peel tabs are first pulled back to beyond the partially covered portion. The first cover sheet is then lifted from the bandage at its end adjacent the pad, and the first cover sheet and the portion of the package on the side of the cover sheet act as the means for applying the bandage to a skin area.

U.S. Pat. No. 4,264,008 discloses an adhesive bandage in which the bandage is folded with the uncoated face of the backing back to back, the folded bandage being covered with a covering material releasably sealed around its periphery and to the adhesive portion of the bandage. Pull tabs at the end of the covering adjacent the fold allow the covering to be opened and the package to act as the means for applying the bandage to a site. The adhesive bandage disclosed in U.S. Pat. No. 4,304,333 operates in a similar manner, the only major difference being that in this case the package has pull tabs at both ends; pull tabs at the end of the package adjacent the ends of the backing strip serve to open the package, while the tabs adjacent the fold serve to apply the bandage.

Other attempts at utilizing the package in a dressing delivery system include, for example, the bandages disclosed in U.S. Pat. Nos. 2,946,435, 2,969,144 and 2,969,145. Despite all such previous attempts, however, a simpler, more efficient system incorporating this concept, as well as a practical means of preparing the delivery system, is still needed. It is therefore the primary objective of the present invention to satisfy this need.

The use of release-retarding means to assist placement of a dressing on a wound area is disclosed in U.S. Pat. No. 4,513,739.

SUMMARY OF THE INVENTION

The present dressing delivery system comprises:

(a) a thin, flexible dressing comprising a backing layer at least partially coated on one side with adhesive and having a pair of ends and a transverse fold such that at least a portion of the uncoated side of the backing layer is adjacent itself;

(b) a protective package enclosing the dressing comprising a pair of layers releasably sealed to each other outside the periphery of the dressing;

(c) a release layer between the adhesive coating of the folded backing layer and the package fixedly attached to the package and split along a line adjacent the fold, the release layer having a substantially greater stiffness and resistance to wrinkling than the dressing;

(d) opening means on the package adjacent the fold; and (e) dressing release-retarding means at each end of the dressing, whereby opening of the package and placement of the dressing on a body portion can be accomplished in a single operation.

Preferably, the dressing is rectangular in form and the fold divides the backing layer into two equal portions. The dressing is preferably breathable, suitably wherein the backing layer is transparent polyurethane film and the adhesive comprises acrylic ester copolymer. The dressing may suitably comprise a central gauze pad, and the adhesive may be water absorbent. In preferred embodiments, the package is paper with the releasable seal of the package being formed with rubber base contact adhesive; the release layer is silicone release coated paper fixedly attached to the package with rubber base contact adhesive; the opening means comprises tabs integral with the package; and the release-retarding means is a strip of the dressing in contact with the package layer.

The present invention also contemplates a method of preparing such a dressing delivery system capable of being opened and placed on a skin area in a single operation, which comprises:

(a) providing a dressing comprising a thin, flexible backing layer at least partially coated on one side with adhesive and having a pair of ends with a protective release layer on the adhesive-coated side of the backing layer, the release layer having a substantially greater stiffness and resistance to wrinkling than the dressing;

(b) folding the protected dressing such that at least a portion of the uncoated side of the backing layer is adjacent itself;

(c) cutting the release layer along a line adjacent the fold in the protected dressing to divide the release layer into two portions;

(d) fixedly attaching each portion of the free side of the release layer to a package layer larger than the folded dressing;

(e) providing each end of the protected dressing with release-retarding means;

(f) releasably sealing the package layers together outside the periphery of the folded dressing; and (g) providing the sealed package layers with opening means at a side adjacent the fold.

While this method of preparation requires each of the operations (a) through (g), the operations are not necessarily performed in the order listed, and may occur simultaneously. For example, operation (c) may be performed before (b) and operation (g) may be performed before (f), while operations (d) and (e) may be performed at the same time.

In preferred forms of the method of the present invention, the protected backing layer is folded into two equal portions; the release layer is cut before the protected dressing is folded and is fixedly attached to the package layer with rubber base contact adhesive, the contact adhesive preferably being applied both to the free side of the release layer and to the package layer before the attachment; a strip of the release layer is removed at each end of the protected dressing to provide the release-retarding means; the package layers are sealed with rubber base contact adhesive; and a portion of the package layers adjacent the fold is left unsealed to provide the opening means.

BRIEF DESCRIPTION OF THE DRAWINGS

The features and advantages of the dressing delivery system of the present invention and its method of preparation will become clear from the following detailed description in conjunction with the following drawings, in which:

FIG. 3 is a bottom plan view of the delivery system of FIGS. 1 and 2 illustrating the opening of the package with the release layer being separated from the dressing;

FIG. 4 is a cross-sectional view of the opening package taken along the line 4—4 of FIG. 3;

FIG. 5 is a side elevational view at that point of placement of the dressing of FIGS. 1 and 2 on a wound;

FIG. 6 is a schematic side elevational view of a packaging machine for assembling the delivery system of FIGS. 1 and 2;

FIG. 6A is an enlarged fragmental cross-sectional view of the starting dressing composite for the delivery system;

FIG. 7 is a partial top plan view of the packaging paper for the delivery system;

FIG. 8 is a pictorial view of the packaging paper shown in FIG. 7, folded;

FIG. 9 is a pictorial view of the packaging paper of FIG. 7 following initial sealing and cutting to provide opening tabs;

FIG. 10 is a pictorial view of the composite dressing for the delivery system having a portion broken away to show contact adhesive on the back side and illustrating die cutting of the composite dressing;

DETAILED DESCRIPTION OF THE INVENTION

Figure 1:
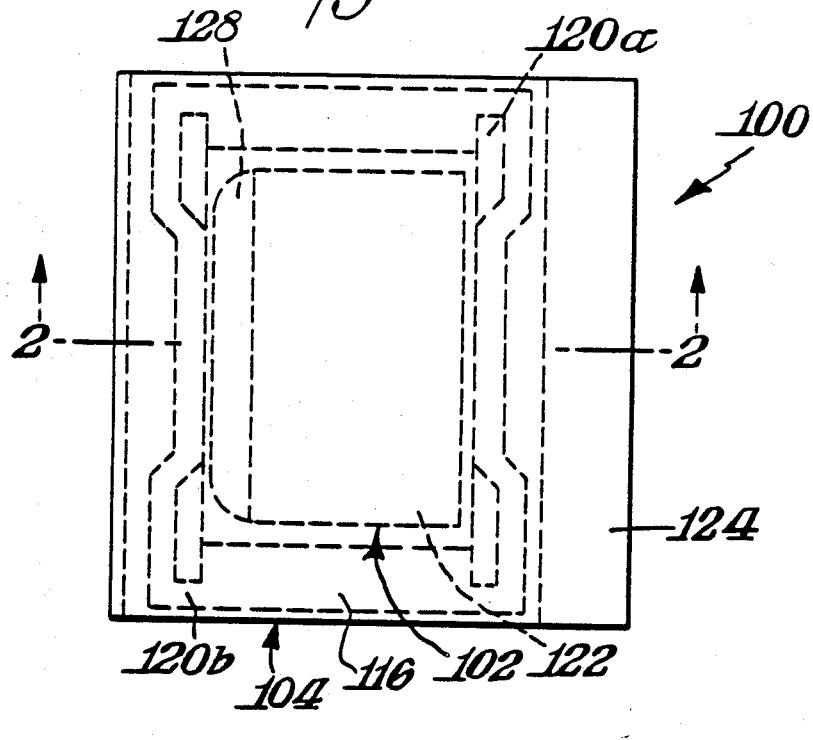
FIG. 1 is a top plan view of a dressing delivery system according to the present invention.
Figure 2:
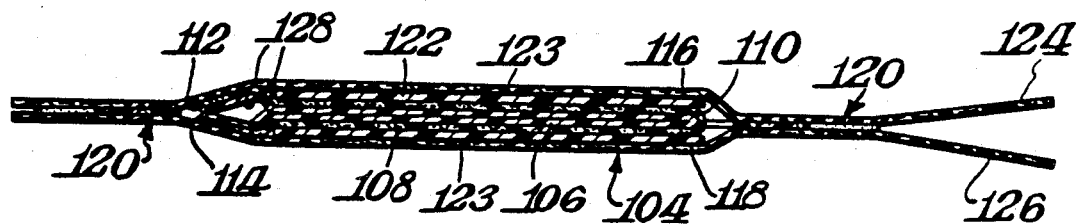
FIG. 2 is a cross-sectional view of the delivery system taken along the line 2—2 of FIG. 1 with the dressing enlarged to more clearly show the individual layers.

A preferred embodiment of the dressing delivery system of the present invention is shown in FIGS. 1 and 2.

This system 100, rectangular in shape, comprises dressing 102 enclosed in protective package 104. Dressing 102 includes backing layer 106 of backing sheet material coated on one side, or face, with pressure-sensitive adhesive 108. Dressing 102 is folded into two equal portions such as to produce a folded dressing of rectangular shape having a single fold 110 and two ends 112, 114 adjacent each other with adhesive 108 facing out and two sections of the uncoated face of backing layer 106 back to back.

Package 104 enclosing dressing 102 comprises a pair of layers 116, 118 which are releasably attached to each other through seal 120 outside the periphery of folded backing layer 106, seal 120 being formed by contact of rubber base contact adhesive pattern 120a on layer 116 with rubber base contact adhesive pattern 120b on layer 118. Release layer 122, in releasable contact with adhesive 108 and fixedly attached to package 104 by means of rubber base contact adhesive 123 as explained hereinafter, serves to protect dressing 102 prior to its application to a wound surface, release layer 122 being split along a line adjacent fold 110 to allow separation of dressing 102 from package 104 during the application. Tabs 124, 126, which serve as the means for opening package 104, are formed from that portion of package 104 which lies outside seal 120 adjacent fold 110, tabs 124 and 126 being an intregal part of package layers 116 and 118, respectively.

Dressing 102 is further provided with release-retarding means 128 at ends 112, 114 to facilitate the application of dressing 102 and prevent its contamination by the applicant. Release-retarding means 128, which offers a greater resistance to separation of dressing 102 from package 104 at ends 112, 114 than over the remainder of dressing 102, may take various forms, such as disclosed in U.S. Pat. No. 4,513,739 which is incorporated herein by reference. Preferably, as shown in FIGS. 1 and 2, the release-retarding means is a strip 128 of dressing 102 at ends 112, 114 in direct contact with layers 116, 118, respectively, the adhesion at strip 128 between dressing 102 and layers 116, 118 being greater than that between the remainder of the dressing 102 and release layer 122.

Backing layer 106 may be of any thin, flexible sheet material suitable for covering a skin wound. Preferably, however, backing layer 106 is a transparent or translucent plastic film which is resistant to water and is breathable, i.e., impermeable to liquids and microbiological contamination but permeable to water vapor and oxygen. Likewise adhesive 108, which preferably coats substantially the entire first face of backing layer 106, is preferably a pressure-sensitive adhesive having similar transparency and permeability characteristics. Such suitable films and adhesives and their preparations are described, for example, in U.S. Pat. No. 3,645,835. These adhesive coated films should preferably have a water vapor transmission rate (WVTR) of at least 250 g/m$^2$/24 hrs (40° C., 80% RH). Especially preferred are such adhesive coated films with a WVTR of about 400 to 500 g/m$^2$/24 hrs in which the backing material is a transparent polyurethane film having a thickness of about 0.5 to 2 mils (13 to 51 microns) and coated with an about 1 mil (25 micron) layer of pressure-sensitive acrylic ester copolymer adhesive.

Within the scope of the present invention is a dressing in which the breathable layer of adhesive coated plastic film is replaced by a backing layer of an impermeable film with moisture-absorbing adhesive mixtures having a moisture absorption rate equal to or greater than the permeability rate of the breathable layer. Such moisture-absorbing mixtures could be in the form of a single adhesive layer contacting the skin or of a second layer coated with a adhesive such as used with the breathable film. Also contemplated is a dressing which combines the breathable and moisture-absorbing features. The dressing might also comprise a central gauze pad.

Release layer 122 may be of any relatively stiff sheet material such as paper, polyethylene or polypropylene which will adequately protect and support dressing 102 and be properly released from adhesive 108. A suitable release material, for example, is a 40 to 75 pound basis weight paper coated on one side with a suitable finish such as clay and with a release agent such as silicone. The thickness of release layer 122 will normally be from about 2 to 6 mils (51 to 152 microns). Likewise, package 104 may be of any sheet material such as paper or polyethylene which will adequately protect dressing 102 from contamination and which will permit steam or chemical vapor sterilization of dressing 102. Seal 120 will normally be provided by a rubber base contact adhesive, although other sealing methods such as heat or electrostatic sealing to releaseably attach layer 116 to layer 118 may be employed, while release layer 122 will normally be fixedly attached to package 104 with rubber base contact adhesive as explained hereinafter.

In use, as shown in FIGS. 3–5, dressing delivery system 100 is grasped at tabs 124, 126 between the thumb and index finger of each of the hands with the system held directly over wound area 130. As the applicant pulls tabs 124, 126 away from each other, package 104 opens and release layer 122 divides into two sections, remaining with package 104 since the adhesion between release layer 122 and package layers 116, 118 is much greater than that between release layer 122 and dressing 102. The separation of dressing 102 occurs with little resistance until it encounters strip 128 at ends 112, 114 where dressing 102 is now firmly but releasably attached only to package layers 116, 118, respectively. At this point, with package 104 now completely open and package layers 116, 118 free of each other, the separation stops until a considerably increased separation force is applied. Dressing 102 is then carefully and easily applied to wound area 130 without wrinkling. A slight tug on each of the tabs 124, 126 separates package layers 116, 118 from dressing 102, and dressing 102 is now firmly in place on wound area 130 without finger contact with adhesive 108 or wrinkling of dressing 102, the entire operation of opening the package 104 and applying the dressing 102 being accomplished in one step.

Preparation of dressing delivery system 100 can be quite simple, using readily available materials and methods. Assembly apparatus 132, shown in FIG. 6, is a preferred apparatus for such preparation, with the state of system 100 at various stages of its preparation being shown in FIGS. 7–12.

Dressing 102, comprising backing layer 106 and pressure-sensitive adhesive 108, is prepared together with release layer 122 in roll form by conventional means, and the combination is passed through an adhesive water suspension to apply a backing 134 of about 5 g/m² of rubber base contact adhesive to the free or back side of release layer 122. The resulting composite 136, shown in FIG. 6A, is then placed on dressing feed roller 138 of assembly apparatus 132.

In another process, a pattern or rubber base contact adhesive such as that applied to the back side of release layer 122 and comprising seal patterns 120a and 120b and center release layer attachment pattern 140 is applied to the underside of a roll of medical package paper 142 printed with ink labelling 144 on its upper side as shown in FIG. 7. The roll of package paper 142 is then placed on package feed roller 146.

Package paper 142 is fed off package feed roller 146 through a pair of creasing rolls 148 which cause package paper 142 to fold in half along crease 150 as shown in FIG. 8. The folded package paper 142 is then sealed by contact of adhesive seal patterns 120a and 120b in that area of package paper 142 between crease 150 and registration line 152 as package paper 142 passes between primary sealing rolls 154; cut at crease 150 by spring-loaded razor 156; and reflattened along registration line 152 as shown in FIG. 9 by power rolls 158 to produce tabs 124, 126.

Composite 136 is fed from dressing feed roller 138 over ink drum 160, which inks margin indicators 162 on the free or back side of backing layer 106 to indicate ends 112, 114 of dressing 102, and then through rotary dies 164, 166. As shown schematically in FIG. 10, die 164 cuts from underneath composite 136 through adhesive backing 134 and release layer 122 only, producing two edge cuts 168 and center cut 170 in release layer 122 and leaving backing layer 106 and adhesive 108 intact. Die 166, on the other hand, cuts from above composite 136 through backing layer 106 and adhesive 108 only, producing a rectangular cut corresponding to dressing 102 of system 100 and comprising transverse side cuts 172 and end cuts 174. The relationship of dies 164 and 166 is such that end cuts 174 produced by die 166 are spaced slightly further apart from each other than are edge cuts 168 produced by die 164. The cut composite 176, free of release layer 122 adjacent end cuts 174, is then transferred by vacuum manifold 178 onto transfer drum 180, while release layer trim 182 is transferred by stripping roll 184 to trim takeup roller 186.

Cut composite 176 is now set for transfer to package paper 142. As an individual unit 188 of cut composite 174, travelling clockwise on transfer drum 180, reaches 12 o'clock, pancake cylinder 190 in conjunction with transfer roll 192 momentarily forces package paper 142 against transfer drum 180, the contact occuring such that center cut 170 of unit 188 is coincident with and centered on a registration line 152 of package paper 142, the speed of transfer drum 180 being regulated by photoelectric control 194 to assure the centering. This action unites adhesive backing 134 of unit 188 with center release layer attachment pattern 140 of package paper 142, thereby fixedly attaching release layer 122 to package paper 142. At the same time, adhesive 108 adjacent end cuts 174 of unit 188 becomes releasably affixed to package paper 142. Since the adhesion between adhesive 108 and package paper 142 is considerably greater than that between adhesive 108 and release layer 122, this attachment adjacent end cuts 174 provides the release-retarding means 128 of system 100.

Figure 11:
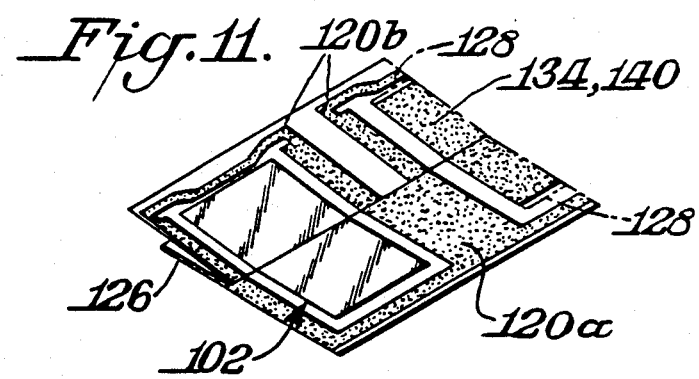
FIG. 11 is a pictorial view of the package open with the dressing of FIG. 10 secured.
Figure 12:
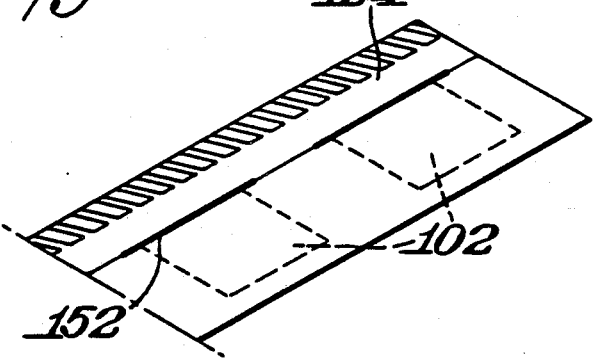
FIG. 12 is a pictorial view of the delivery system closed and sealed.

The condition of dressing delivery system 100 at the point of attachment of unit 188 to package paper 142 is shown pictorally in FIG. 11. This combination is fed through power rolls 196, then through secondary sealing rolls 198 to completely seal package layers 116 and 118 together at the point of contact of edge adhesive portions 140a and 140b with each other as shown in FIG. 12. Package paper 142 is then cut with rotary shear 200 to provide individual units of system 100 which are collected in holding box 202. System 100 is finally sterizilized by conventional techniques and is ready for use. What is claimed is:

1. A dressing having a delivery system to facilitate application of the dressing onto a human which comprises:
   (a) a thin flexible backing layer having a suitable adhesive on substantially all of one surface thereof and a central pad on the adhesive coated surface of the backing layer, the adhesive being impermeable to liquids, but permeable to water vapor and oxygen, and a pair of ends and a transverse fold such that at least a portion of the non-adhesive coated side of the backing layer is adjacent itself;
   (b) a protective package enclosing the dressing comprising a pair of layers releasably sealed to each other outside the periphery of the dressing;
   (c) a release layer between the adhesive of the folded backing layer and the package fixedly attached to the package and split along a line adjacent the fold, the release layer having a substantially greater stiffness and resistance to wrinkling than the dressing;
   (d) opening means on the package adjacent the fold; and
   (e) dressing release-retarding means at each end of the dressing.

2. A dressing according to claim 1 wherein the pad is centrally disposed on the adhesive coated side of the backing layer.

3. A dressing according to claim 2 wherein the pad is a gauze pad.

4. A dressing according to claim 1 in rectangular form.

5. A dressing according to claim 1 wherein the dressing is breathable.

6. A dressing according to claim 1 wherein the adhesive is an acrylic ester copolymer.

7. A dressing according to claim 1 wherein the adhesive is water absorbant.

8. A dressing according to claim 1 wherein the package is paper and the release layer is silicon release coated paper fixedly attached to the package with a suitable adhesive.

9. A dressing according to claim 1 wherein the opening means comprises tabs integral with the package.

10. A dressing according to claim 1 wherein the release-retarding means is a strip of the dressing in contact with a package layer.

11. A dressing according to claim 1 wherein the backing layer is impermeable to water, vapor and oxygen.

12. A dressing according to claim 1 wherein the backing layer is a transparent polyurethane film.

* * * * *